United States Patent
Eror et al.

(10) Patent No.: US 8,121,677 B2
(45) Date of Patent: *Feb. 21, 2012

(54) METHOD FOR DIAGNOSING A DISEASE

(75) Inventors: Steven C. Eror, Salt Lake City, UT (US); Lynn H. Satterthwaite, North Ogden, UT (US)

(73) Assignee: Fresh Medical Laboratories, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/578,329

(22) Filed: Oct. 13, 2009

(65) Prior Publication Data

US 2010/0094160 A1    Apr. 15, 2010

Related U.S. Application Data

(63) Continuation of application No. 11/978,045, filed on Oct. 25, 2007, now Pat. No. 7,603,171.

(51) Int. Cl.
*A61B 5/05* (2006.01)

(52) U.S. Cl. ..................................................... 600/547

(58) Field of Classification Search .............. 600/547; 73/105; 250/306, 307; 977/873
See application file for complete search history.

(56) References Cited

U.S. PATENT DOCUMENTS

| | | | |
|---|---|---|---|
| 7,603,171 B2 * | 10/2009 | Eror et al. ...................... | 600/547 |
| 2002/0183645 A1 * | 12/2002 | Nachaliel ...................... | 600/547 |
| 2004/0204658 A1 | 10/2004 | Dietz et al. | |
| 2005/0015017 A1 | 1/2005 | Horne et al. | |
| 2006/0020223 A1 | 1/2006 | Horne et al. | |
| 2007/0239061 A1 | 10/2007 | Carter et al. | |

OTHER PUBLICATIONS

Notice of Allowance and Fees Due mailed Jun. 3, 2009 in U.S. Appl. No. 11/978,045, filed Oct. 25, 2007.
Office Action mailed Feb. 24, 2009 in U.S. Appl. No. 11/978,045, filed Oct. 25, 2007.
Office Action mailed Nov. 6, 2008 in U.S. Appl. No. 11/978,045, filed Oct. 25, 2007.
Office Action mailed May 28, 2008 in U.S. Appl. No. 11/978,045, filed Oct. 25, 2007.
Peter Åberg et al.; Skin Cancer Identification Using Multifrequency Electrical Impedance—A Potential Screening Tool; IEEE Transactions on Biomedical Engineering, vol. 51, No. 12, Dec. 2004.
V. Cherepenin et al.; Preliminary static EIT images of the thorax in health and disease; Physiological Measurement 2002, 23: 33-41.
A. Malich et al.; Use of electrical impedance scanning in the differentiation of sonographically suspicious and highly suspicious lymph nodes of the head-neck region; Eur Radiol, 2002, 12:1114-1120.

(Continued)

*Primary Examiner* — Brian Szmal
(74) *Attorney, Agent, or Firm* — Stoel Rives LLP; Matthew D. Thane

(57) ABSTRACT

Methods, systems, and apparatus to determine the presence of a disease condition in a medical patient by evaluating conductivity information. In some embodiments, point-attributes values may be obtained from conductivity data sets. This data may be compared to previously determined data, such as threshold values. In some embodiments, z-scores may be determined to combine a plurality of point-attribute values in formulation of a composite score for a patient. In some embodiments, z-scores may be weighted by overall accuracy of the point-attribute in predicting presence of the disease.

20 Claims, 7 Drawing Sheets

OTHER PUBLICATIONS

A Malich et al.; Additional value of electrical impedance scanning: experience of 240 histologically-proven breast lesions; European Journal of Cancer, 37 (2001) 2324-2330.

Hans-Joachim Mentzel et al.; Electrical impedance scanning—application of this new technique for lymph node evaluation in children; Pediatr Radiol (2003) 33:461-466.

Alexander Stojadinovic et al.; Electrical Impedance Scanning for the Early Detection of Breast Cancer in Young Women: Preliminary Results of a Multicenter Prospective Clinical Trial; Journal of Clinical Oncology, vol. 23, No. 12 (Apr. 20, 2005).

Herman P Schwan; The Practical Success of Impedance Techniques from an Historical Perspective; Ann NYAS 1999; 873:1-12.

Alexander Stojadinovic et al.; Electrical Impedance Scanning of Thyroid Nodules Before Thyroid Surgery: A Prospective Study; Annals of Surgical Oncology; 12(2):152-160 (Nov. 2, 2005).

Shah R. et al.; Results of Surgical treatment of stage I and II lung cancer; 37(2):169-72 (Apr. 1996).

Jonathan C. Nesbitt et al.; Survival in Early-Stage Non-Small Cell Lung Cancer; The Annals of Thoracic Surgery; 60:466-472 (1995).

BJ Flehinger et al.; The effect of surgical treatment on survival from early lung cancer. Implications for screening; Chest; 101:1013-1018 (1992).

Digant Gupta et al.; Bioelectrical impedance phase angle as a prognostic indicator in advanced pancreatic cancer; British Journal of Nutrition; 92:957-962 (2004).

Stephen J. Swensen et al.; CT Screening for Lung Cancer: Five-year Prospective Experience; Radiology; 235:259-265 (2005).

Silvia Toso et al.; Bioimpedance Vector Pattern in Cancer Patients Without Disease Versus Locally Advanced or Disseminated Disease; Nutrition; 19:510-514 (2003).

Food and Drug Administration Approval—TransScan (T-Scan 2000) (Apr. 1999).

Silvia Toso et al.; Altered Tissue Electric Properties in Lung Cancer Patients as Detected by Bioelectric Impedance Vector Analysis; Nutrition; 16:120-124 (2000).

Brian H. Brown et al.; Detection of cervical intraepithelial neoplasia using impedance spectroscopy: a prospective study; BJOG: an International Journal of Obstetrics and Gynaecology; vol. 112, pp. 802-806 (Jun. 2005).

* cited by examiner

| Measurement Sequence | Data Acquisition Point | Measurement Sequence | Data Acquisition Point |
|---|---|---|---|
| 1 | FML-1aTR | 32 | FML-1aTL |
| 2 | FML-1bTR | 33 | FML-1bTL |
| 3 | FML-1cTR | 34 | FML-1cTL |
| 4 | FML-2aTR | 35 | FML-2aTL |
| 5 | FML-1R | 36 | FML-1L |
| 6 | FML-2aR | 37 | FML-2aL |
| 7 | FML-2bR | 38 | FML-2bL |
| 8 | FML-2cR | 39 | FML-2cL |
| 9 | FML-3aR | 40 | FML-3aL |
| 10 | FML-3bR | 41 | FML-3bL |
| 11 | FML-4R | 42 | FML-4L |
| 12 | FML-5R | 43 | FML-5L |
| 13 | FML-6aR | 44 | FML-6aL |
| 14 | FML-6dR | 45 | FML-6dL |
| 15 | FML-6eR | 46 | FML-6eL |
| 16 | FML-7aR | 47 | FML-7aL |
| 17 | FML-7bR | 48 | FML-7bL |
| 18 | FML-7cR | 49 | FML-7cL |
| 19 | FML-8aR | 50 | FML-8aL |
| 20 | FML-8bR | 51 | FML-8bL |
| 21 | FML-8cR | 52 | FML-8cL |
| 22 | FML-8dR | 53 | FML-8dL |
| 23 | FML-8eR | 54 | FML-8eL |
| 24 | FML-8fR | 55 | FML-8fL |
| 25 | FML-9R | 56 | FML-9L |
| 26 | FML-10R | 57 | FML-10L |
| 27 | FML-11aR | 58 | FML-11aL |
| 28 | FML-11bR | 59 | FML-11bL |
| 29 | FML-12aR | 60 | FML-12aL |
| 30 | FML-12bR | 61 | FML-12bL |
| 31 | FML-12cR | 62 | FML-12cL |

FIG. 7

| Attribute | Direction of low conductivity | Overall Accuracy % | Point with side | ODA Classification Rule | ODA low conductivity study arm** |
|---|---|---|---|---|---|
| AUC from 0 slope | low | 85.71 | FML2bR | IF ≤0.495 THEN 2* | 2 |
| AUC from 0 slope | low | 85.71 | FML6aL | IF ≤0.587 THEN 2 | 2 |
| AUC from 0 slope | low | 85.71 | FML1R | IF ≤0.7 THEN 2 | 2 |
| AUC from 0 slope | low | 85.71 | FML8aR | IF ≤0.545 THEN 2 | 2 |
| AUC total | low | 85.71 | FML2bR | IF ≤0.4515 THEN 2 | 2 |
| AUC total | low | 92.86 | FML6aL | IF ≤0.512 THEN 2 | 2 |
| AUC total | low | 85.71 | FML1R | IF ≤0.6285 THEN 2 | 2 |
| AUC total | low | 92.86 | FML2aR | IF ≤0.5395 THEN 2 | 2 |
| AUC total | low | 85.71 | FML8aR | IF ≤0.4745 THEN 2 | 2 |
| AUC to 0 slope | low | 85.71 | FML8fL | IF ≤0.442 THEN 1 | 1 |
| AUC to 0 slope | low | 85.71 | FML2bL | IF ≤0.471 THEN 2 | 2 |
| AUC to 0 slope | low | 85.71 | FML2bR | IF ≤0.4395 THEN 2 | 2 |
| AUC to 0 slope | low | 85.71 | FML6dL | IF ≤0.473 THEN 2 | 2 |
| AUC to 0 slope | low | 92.86 | FML8aR | IF ≤0.452 THEN 2 | 2 |
| base drop | high | 85.71 | FML12aL | IF ≤2.5 THEN 2 | 1 |
| base max | low | 85.71 | FML8fR | IF ≤60.5 THEN 2 | 2 |
| base max | low | 85.71 | FML2bR | IF ≤49.5 THEN 2 | 2 |
| base max | low | 85.71 | FML6aL | IF ≤59.0 THEN 2 | 2 |
| base max | low | 85.71 | FML1R | IF ≤70.0 THEN 2 | 2 |
| base max | low | 85.71 | FML8aR | IF ≤54.5 THEN 2 | 2 |
| base min | low | 85.71 | FML2bR | IF ≤49.5 THEN 2 | 2 |
| base min | low | 85.71 | FML6aL | IF ≤58.5 THEN 2 | 2 |
| base min | low | 85.71 | FML1R | IF ≤70.0 THEN 2 | 2 |
| base min | low | 85.71 | FML8aR | IF ≤54.5 THEN 2 | 2 |
| base rise | low | 85.71 | FML8cR | IF ≤41.0 THEN 1 | 1 |
| base rise | low | 92.86 | FML2bL | IF ≤21.0 THEN 2 | 2 |
| base rise | low | 85.71 | FML3bL | IF ≤21.5 THEN 2 | 2 |
| base rise | low | 85.71 | FML8bL | IF ≤30.0 THEN 2 | 2 |
| base rise | low | 85.71 | FML12cL | IF ≤38.5 THEN 2 | 2 |
| base rise | low | 85.71 | FML11aL | IF ≤30.5 THEN 2 | 2 |

FIG. 8

METHOD FOR DIAGNOSING A DISEASE

RELATED APPLICATIONS

This application is a continuation of application Ser. No. 11/978,045, filed Oct. 25, 2007, and titled "Method for Diagnosing a Disease," which is incorporated herein by specific reference.

BACKGROUND

1. Field of the Invention

This invention relates generally to diagnosis of a disease condition in a mammal. It is particularly directed to detecting lung cancer in a human by evaluating bioelectrical measurements taken between discreet points on the subject human body.

2. State of the Art

By definition, electrical impedance is the ratio of the voltage difference to the current across a circuit or a body (Ohm's law), and conductance is the inverse of impedance (1/impedance). The dielectric properties of human cells and tissue are widely recognized and are essential for several diagnostic procedures currently in use. The Coulter Counter for electronic cell counting, the electrocardiogram for assessing cardiac functioning, and the encephalogram for evaluating brain functioning are some common examples.

The dielectric properties of the human body are well-characterized in literature and provide the basis for several clinical tests including electrocardiography, electroencephalography, plethysmography, electrical conductance tomography and BIA. Moreover, there is clear evidence that cancerous tissues differ in their bioelectrical conductance properties compared to those of benign and adipose tissue, and a device using bioelectrical conductance measurements has been approved by the United States Food and Drug Agency for use as a diagnostic adjunctive to mammography in the work-up of breast cancer in women under 40 years of age. The same technology is currently being evaluated as a screening test. Investigations have also been conducted for various other malignancies including cervical, skin, lymph nodes, thyroid, and lung cancer. In the bioelectrical assessment of lung cancer, there is evidence that electrical impedance tomography is capable of imaging the lungs, however limited information exists concerning the most effective access points and the modalities for bioelectrical conductivity measurement.

Many clinical investigations have examined the potential of using electrical properties for aiding in cancer diagnosis. Aberg and colleagues reported on the use of electrical bioconductance to assess skin cancers. They found separation of malignant melanoma and non-melanoma skin cancer from benign nevi with 75% and 87% specificity, respectively, and 100% sensitivity for both. This was considered equal to, or better than, conventional visual screening. Electrical conductance scanning also shows promise in lymph node evaluation in children and adults. Malich et al reported that of 106 sonographically suspicious lymph nodes in the head and neck region, electrical conductance scanning was able to detect 62 of 64 malignant nodes for a true positive rate of 96.9%. However in this study, only 19 of 42 inflammatory benign lymph nodes were correctly identified as benign for a true negative rate of 45.2%. The authors conclude that while these results are promising, further development work is needed to reduce the high number of false-positives. Similar results were reported when potentially malignant lymph nodes were evaluated in children using electrical conductance. Another recent prospective study of electrical conductance scanning of 64 patients who were undergoing surgery for possible thyroid malignancies found that it is a potentially useful imaging modality for differentiating thyroid neoplasms.

Breast cancer has probably been studied the most extensively with conductance technology. Investigations of electrical conductance scanning in patients with sonographically or mammographically suspicious lesions found that there were significant differences between the tissues of normal and abnormal subjects. By considering electrical conductance results in addition to ultrasound and mammography, the sensitivity of cancer detection increased from 86% to 95%. In 1999, the US FDA approved a multi-frequency conductance breast scanner (T-Scan 2000) for use as an adjunct to mammography for select patients. A recent study of the T-Scan 2000ED which used a modified algorithm provided preliminary evidence that electrical conductance scanning might be valuable for early detection of breast cancer in young women at increased risk for having disease at the time of scanning.

Other recent investigations have shown that conductance spectroscopy may be a viable screening tool for detection of cervical cancer. Additional studies in humans demonstrated altered electrical properties in tissues of patients with various cancers including lung, pancreas and colorectal compared to those without cancer. Several of these studies have been done in lung cancer patients providing evidence that alterations in bioelectrical conductance are evident in this patient population.

Although there is clear evidence that survival is increased by resection and oncolytic intervention of earlier stage lung cancer, detection at the earlier stages remains difficult. The current interest and ongoing investigation of using low-dose CT scanning for screening presents challenges as well. It is almost universally agreed that CT scanning of high risk subjects identifies nodules that qualify for further clinical evaluation, either by repeat CT scan or biopsy, and yet 92-96% of identified lesions will be found to be benign. As a result, the economic and health costs associated with using CT scan in this modality is not offset by clinical benefit.

Consequently, there is a long felt need for a non-significant risk, non-invasive technology that could be utilized in conjunction with CT scanning to further differentiate suspicious masses or nodules identified by CT. Such differentiating information desirably would be clinically meaningful in identifying which patients should proceed for further diagnostic evaluation and those that are likely to have a benign finding.

BRIEF SUMMARY OF THE INVENTION

This invention may be embodied to provide a method to diagnose lung cancer in a medical patient. One embodiment of a workable method includes providing a measurement device operable to measure conductivity between a first reference point and a first interrogation point on the body of a patient. The conductivity is then measured, between that first reference point and a first interrogation point, to obtain a first data-set as a function of time and over a period of time. Then, at least one attribute value obtained from the first data-set is compared to a previously determined corresponding attribute threshold in a table look-up operation to determine if the patient has lung cancer.

Such a method may also include measuring the conductivity, between the first reference point and a first plurality of interrogation points, to obtain a first plurality of data-sets, each such data-set comprising conductivity values as a function of time and over a period of time. Then, the plurality of point-attribute values obtained from the first plurality of data-sets are compared to corresponding previously determined attribute thresholds in a table look-up operation to determine if the patient has lung cancer.

Desirably, the measurement device is structured and arranged to provide computer control of contact pressure between its measurement electrode tip and the surface of the subject's body at an interrogation point. It is currently preferred that the computer control incorporates real-time conductivity measurement in a feedback loop effective to adjust the contact pressure at the probe tip. Further, the method can include measuring the conductivity, between a second reference point and a second plurality of interrogation points, to obtain a second plurality of data-sets, each such data-set comprising conductivity values as a function of time and over a period of time. In such case, the plurality of point-attribute values obtained from the second plurality of data-sets may be compared to corresponding previously determined attribute thresholds in a table look-up operation to determine if the patient has lung cancer.

In one operable method according to certain principles of the instant invention, the sum of the first plurality of interrogation points and the second plurality of interrogation points populate at least three point-attributes for use in the comparing step. In another operable method, the sum of the first plurality of interrogation points and the second plurality of interrogation points populate at least twelve point-attributes for use in the comparing step. In another operable method, the sum of the first plurality of interrogation points and the second plurality of interrogation points populate at least thirty point-attributes for use in the comparing step.

The comparison step may include developing a composite score for a patient by converting a portion of obtained point-attribute values to corresponding z-scores, and combining the z-scores. Sometimes, developing the composite score includes applying a previously determined overall accuracy of each point-attribute for indicating presence of cancer in a population of patients by weighting each z-score by its corresponding overall accuracy.

The invention may be embodied as a method to determine a rule-set for point-attribute data effective to diagnosis a disease condition in a patient. One such method includes: providing a first arm group of medical patients that have been diagnosed with the disease; providing a second arm group of medical patients that are free from the disease; obtaining a plurality X of data-sets corresponding to respective time-based conductivity measurements between similar points on the body of each patient; parsing the data-sets to determine a plurality Y of attributes, each attribute being effective to characterize a portion of a plot of a time-based conductivity measurement; expanding X data-sets by Y attributes to obtain $(X)*(Y)$ point-attributes; determining if a threshold value exists for each point-attribute that would predict, above a threshold criteria, if a patient whose measured point-attribute value is compared to the threshold value would be in the first arm group or in the second arm group; discarding from further consideration each point-attribute for which such a threshold value can not be determined; retaining for further consideration at least one point-attribute for which such a threshold value can be determined; and populating the rule-set by the threshold value corresponding to each attribute at each retained point-attribute where the threshold criteria is satisfied.

The method to determine a rule-set may also include developing a composite score for a patient by converting a portion of retained point-attribute data to corresponding z-scores to develop an overall prediction score. Sometimes, overall accuracy of each point-attribute for indicating presence of the disease condition is pre-determined; and computation of the composite score includes weighting each z-score by its corresponding overall accuracy.

Measurements typically include conductivity measurements made between a first reference point disposed on one lateral side of the body of each patient in both the first arm group and the second arm group and a plurality of interrogation points distributed over an area of that body. Measurements may also include conductivity measurements made between a second reference point disposed on the other lateral side of the body of each patient in both the first arm group and the second arm group and a plurality of interrogation points distributed over an area of that body. Measurements may also be taken at a midline portion of a subject's body. Typically, the measured conductivity data is recorded blind to a patient's membership in an arm group. However, determination of accuracy and threshold values is made having visibility to a patient's membership in an arm group.

The method to determine a rule-set may include determining potential disease sidedness and discarding all opposite-side point-attribute data based upon disease side-bias.

The invention may also be embodied as a system adapted to assist in making a diagnosis of a disease condition in a medical patient. One operable such system includes a computer assembly including a processor, a memory, and a display terminal. Software is loaded into the memory as program comprising an instruction set. A measurement device is disposed in communication with the computer assembly and is operable to measure conductivity of the body of the patient between a ground point and a measurement point. Desirably, the measurement device is capable of measuring conductivity as a function of time, and over a period of time, to obtain a conductivity data-set corresponding to each such measurement. Typically, the processor is programmed to extract point-attribute values from at least one data-set. Then, the processor compares at least one attribute value obtained from a data-set to a previously determined corresponding attribute threshold in a table look-up operation. Often a portion of obtained point-attribute values are converted to corresponding z-scores to permit their combination into a composite score. Certain composite scores include weighting each z-score by its corresponding predetermined corresponding overall accuracy before combining each weighted z-score to develop a composite score for a patient.

The system desirably includes a measurement device structured and arranged to provide computer control of contact pressure between its measurement electrode tip and the surface of the subject's body at a measurement point. One operable form of computer control includes real-time conductivity measurement in a feedback loop effective to adjust the pressure.

A currently preferred software program causes display of visible prompts on the display terminal corresponding to ground and measurement points to assist a clinician in placement of the interrogation electrode on the subject's body. Desirably, the system is adapted to confirm validity of a measured data collection event. In certain such cases, the system may cause user perceptible feedback corresponding to completion of obtaining a valid data collection event.

BRIEF DESCRIPTION OF THE DRAWINGS

In the drawings, which illustrate what are currently considered to be the best modes for carrying out the invention:

FIG. 7 is a table listing certain interrogation point locations that may be operable for use in detecting or diagnosing a disease.

FIG. 8 is a table containing point-attribute data obtained in accordance with one implementation of the invention.

BRIEF DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

Figure 1:
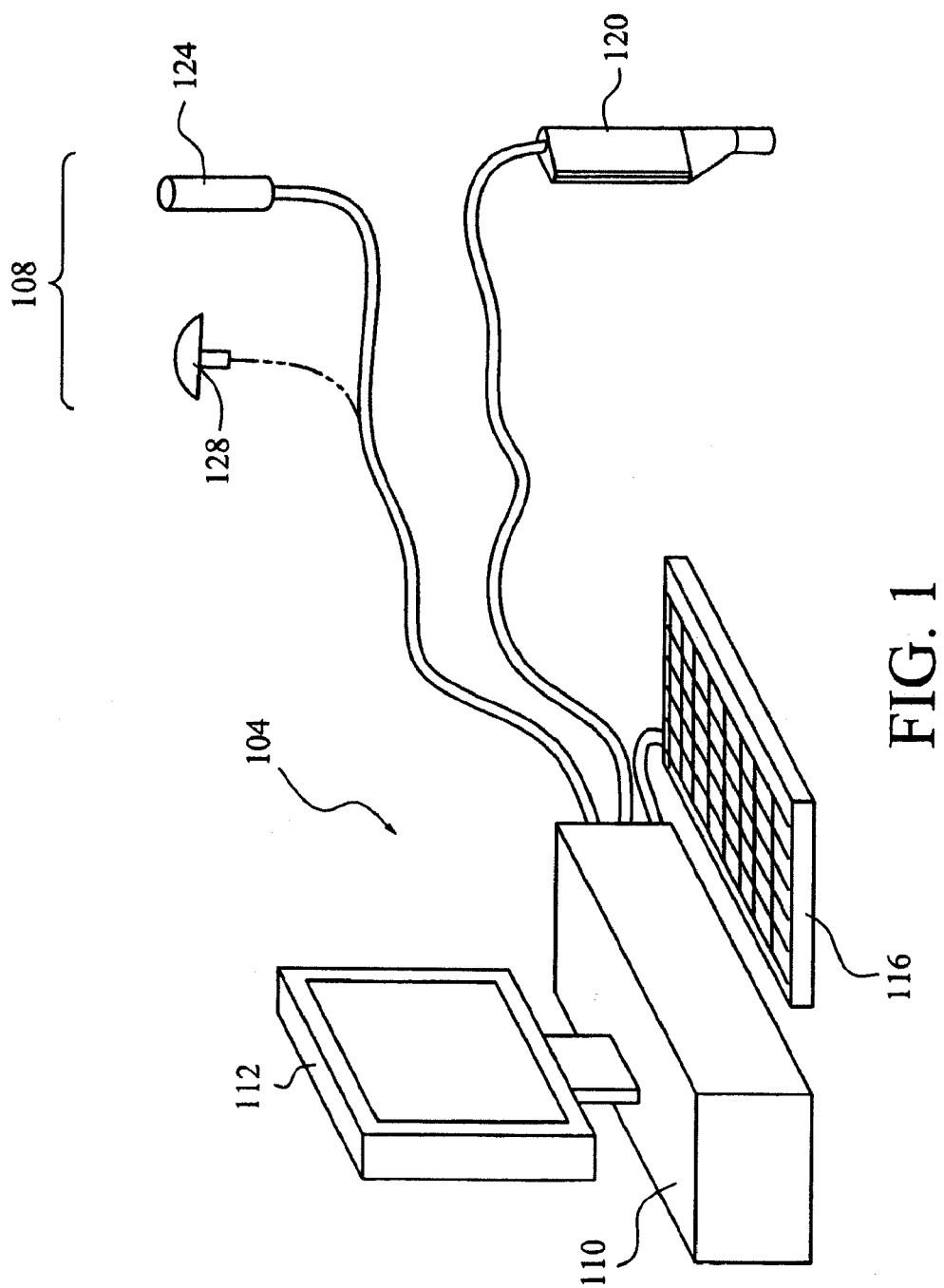
FIG. 1 is a view in perspective of a measurement system operable for use in a method according to certain principles of the instant invention.

A currently preferred embodiment of a device, generally indicated at 100, operable in practice of a method according to certain principles of the instant invention is illustrated in FIG. 1. Device 100 includes a computer assembly, generally indicated at 104, and a probe system, generally indicated at 108. The computer assembly 104 typically includes a housing 110 to contain a processor and memory in communication with a display device, such as monitor 112, One or more input device, such as illustrated keyboard 116, a mouse, or the like, may also be included in operable association with the computer assembly. Similarly, an output device, such as a printer, USB port, network connector, media writer, and the like, may be disposed in operable relation with a computer system 104.

The probe system 108 typically includes an interrogation electrode 120. A currently preferred interrogation electrode is disclosed in United States Patent Application Publication No. 2005/0015017, published Jan. 20, 2005, the entire contents of which are hereby incorporated by this reference. Desirably, an interrogation electrode 120 will be structured to permit computer controlled application of electrode contact pressure force onto a subject's skin during a measurement sequence. Such computer control desirably includes a feedback loop encompassing real-time conductivity data as measured by the probe itself.

Probe system 108 also includes a reference electrode, such as cylinder 124 that may be hand-held by a subject, or optional spot-probe 128 that may be applied by the clinician. Desirably, the reference electrodes are structured to contact a relatively larger area of a measured subject's skin, and isolate the operator from the formed electrical circuit. An operable electrode 124 includes a cylindrical mass of conductive material, such as metal, sized about 1 inch in diameter, and about 3 inches in length. Brass is an operable metal from which to form a reference electrode, although other metals and conductive materials are also operable. An operable spot-probe 128 may be formed as a blunt, generally mushroom-shaped, mass of conductive material, such as metal, including brass. The electrodes are placed into electrical communication with conductivity measuring equipment that may conveniently be contained in housing 110 for communication of electrical conductivity data to the computer system 104.

Water is typically sprayed on a subject's hand, and the cylindrical reference electrode 124 is held in the moistened palm of a clenched fist. Sometimes, a strap may be applied to ensure the hand does not inadvertently open, or lose contact with the electrode 124. The round reference electrode 128 is placed in specific locations on the back of the subject by the operator using moisture. The operator handles the electrode with gloves to maintain electrical isolation, and applies uniform pressure during the measurement.

Figure 2:
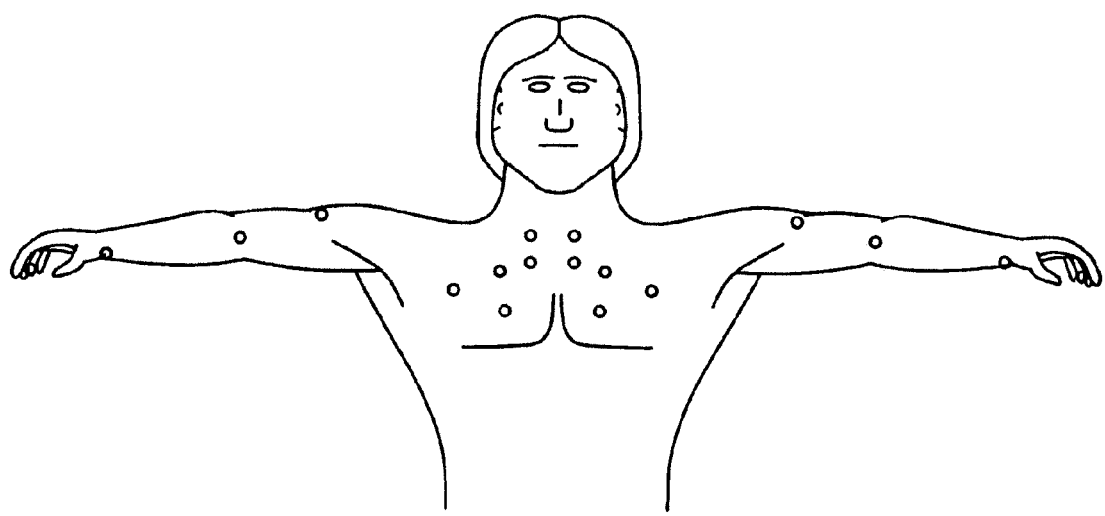
FIG. 2 is a front view in elevation of the torso of a medical patient illustrating certain interrogation points at which a probe tip may be placed to make one or more conductivity measurements in practice of a method according to certain principles of the instant invention.
Figure 3:
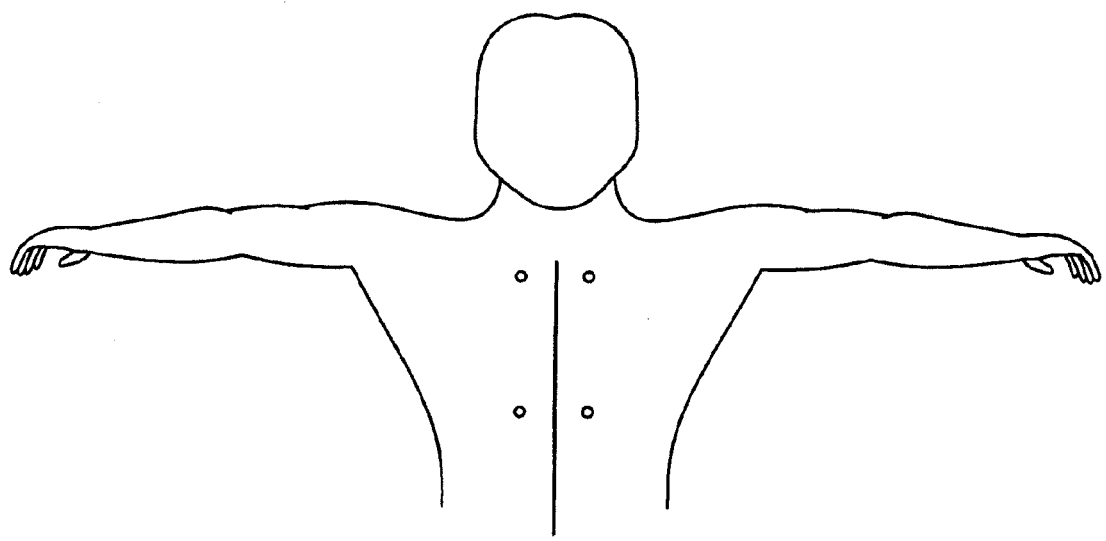
FIG. 3 is a rear view in elevation of the torso of a medical patient illustrating certain interrogation points at which a probe tip may be placed to make one or more conductivity measurements in practice of a method according to certain principles of the instant invention.

Data acquisition includes measuring conductivity as a function of time, and over a period of time, between a reference electrode disposed at one or more reference point, and an interrogation electrode disposed, typically, at each of a plurality of interrogation points. Certain interrogation point locations that may be operable for use in detecting lung cancer are located on the arms, upper arms, shoulder, chest, and back, and are listed in the table of FIG. 7 under Data Acquisition Point. FIGS. 2 and 3 illustrate certain selected electrode point locations. Typically, the reference electrode 124 will be held in the subject's hand on an opposite side of the body midline from the interrogation point during data acquisition for detection of lung cancer. That is, in such case, and for interrogation points having a label ending with "R", the reference electrode 124 will be held in the subject's left hand, and vice versa. Exceptions to this generalization are indicated in the following detailed descriptions of point locations.

FML-1R is located between costa 3 and costa 4 at 1.5 thumb-widths lateral to the midpoint between the spinous process of the second and third thoracic vertebra.

FML-1aTR is located on the 2nd rib approximately 2½ thumb widths lateral from the midline or depression point on the sternum. NOTE: Use the round reference electrode and place it at FML-1R.

FML-1bTR is located in the 2nd intercostal space on a line between the lateral insertion of the sternocleidomastoid muscle and the nipple. It is approximately 3-3½ thumb widths from the midline. NOTE: Use the round reference electrode and place it at FML-1R.

FML-1cTR is located in the 3rd intercostal space approximately 3½ thumb widths lateral from the midline. NOTE: Use the round reference electrode and place at FML-1R.

FML-2aTR is located in the depression on the lower border of the clavicle, 2 thumb-widths lateral to the midline. The 2 thumb-width line is located midway between the midline and the mamillary line. NOTE: Use the round reference electrode and place it 2 thumb-widths lateral to the midline of the spine on the back in the lowest intercostal space.

FML-2aR is located in the depression on the lower border of the clavicle, 2 thumb-widths lateral to the midline. The 2 thumb-width line is located midway between the midline and the mamillary line.

FML-2bR is located on the lateral aspect of the chest, in the first intercostal space, 6 thumb-widths lateral to the midline, 1 thumb-width inferior to FML-2c.

FML-2cR is located on the antero-lateral aspect of the chest, below the lateral extremity of the clavicle, 6 thumb-widths lateral to the midline, in the center of the hollow of the delto-pectoral triangle. Ask the patient to extend their hand forwards while you apply resistance to their hand, in order to emphasize the delto-pectoral triangle, and locate FML-2c at its center.

FML-3aR is located on the antero-lateral aspect of the upper arm, 3 thumb-widths inferior to the axillary fold and 6 thumb-widths superior to FML-4, in the depression between the lateral border of the biceps brachii muscle and the shaft of the humerus.

Divide the distance between the axillary fold and the cubital crease of the elbow into equal thirds. FML-3a is at the junction of the upper and middle third.

FML-3bR is located on the antero-lateral aspect of the upper arm, 4 thumb-widths inferior to the axillary fold and 5 thumb-widths superior to FML-4, in the depression between the lateral border of the biceps brachii muscle and the shaft of the humerus.

FML-4R is located on the cubital crease of the elbow, in the depression at the radial side of the tendon of biceps brachii.

FML-5R is located by moving from the wrist up the forearm along the flexor carpi radialis to the point where the brachioradialis is encountered.

FML-6aR is located on the radial artery, approximately 2½ inches above the wrist crease or 1 inch above the beginning of the styloid process of the radius bone. It is at the junction formed by the tendon of the brachioradialis and the flexor digitirum superficialis muscles.

FML-6dR is located approximately 1 inch proximal from the distal transverse wrist crease on the medial edge of the styloid process of the radius (palmar aspect of the hand).

FML-6eR is located at the lateral end of the distal wrist crease at the base of the palm. It is directly proximal to the lateral edge of the scaphoid's tubercle.

FML-7aR is located between the scaphoid and trapezium bones directly distal to the tubercle of the scaphoid FML-7bR is located at the proximal diaphyseal end of the first metacarpal bone, palmar aspect of the hand.

FML-7cR is located at the distal diaphyseal end of the 1st metacarpal bone on its ulnar side (palmar surface of the hand).

FML-8aR is located between the radius and navicular bones on the ulnar side of the extensor pollicis longus tendon.

FML-8bR is located at the distal diaphyseal end of the proximal phalanx of the thumb on its radial side. It is measured on a 45 degree angle with the probe pointing distally.

FML-8cR is located at the proximal diaphyseal end of the metacarpal phalanx of the thumb on its ulnar side (dorsal aspect of the hand). It is measured on a 45-degree angle with the probe pointing proximally.

FML-8dR is located at the distal diaphyseal end of the basal (proximal) phalanx of the thumb on its ulnar side (dorsal aspect of the hand). It is measured on a 45-degree angle with the probe pointing distally.

FML-8eR is located at the proximal diaphyseal end of the distal phalanx of the thumb (dorsal aspect). It is measured on a 45-degree angle with the probe pointing proximally.

FML-8fR is located at the distal diaphyseal end of the nail phalanx of the thumb on its ulnar side. It is measured on a 90-degree angle on the side of the finger with the probe on a horizontal plane with that of the fingernail.

FML-9R is located at the proximal diaphyseal end of the middle phalanx of the second finger on its ulnar side (dorsal aspect of the hand). It is measured on a 45 degree angle with the probe pointing proximally.

FML-10R is located at the proximal diaphyseal end of the middle phalanx of the 3rd finger on its radial side (dorsal aspect of the hand). It is measured on a 45 degree angle with the probe pointing proximally.

FML-11aR is located at the distal diaphyseal end of the ungual phalanx of the 4th finger on its ulnar side (dorsal aspect of the hand). It is measured on a 90 degree angle on the side of the finger.

FML-11bR is located at the proximal diaphyseal end of the middle phalanx of the 4th finger on its ulnar side (dorsal aspect of the hand). It is measured on a 45 degree angle with the probe pointing proximally.

FML-12aR is located at the distal diaphyseal end of the proximal phalanx of the little (5th) finger on its radial side (dorsal aspect of the hand). It is measured on a 45 degree angle with the probe pointing distally.

FML-12bR is located at the proximal diaphyseal end of the basal phalanx of the 5th finger on its ulnar side. It is measured on a 45 degree angle with the probe pointing proximally.

FML-12cR is located at the distal diaphyseal end of the nail phalanx of the 5th finger on its ulnar side (dorsal aspect of the hand). It is measured on a 90 degree angle on the side of the finger with the probe on a horizontal plane with that of the fingernail.

FML-1L is located between costa 3 and costa 4 at 1.5 thumb-widths lateral to the midpoint between the spinous process of the second and third thoracic vertebra.

FML-1aTL is located on the 2nd rib approximately 2½ thumb widths lateral from the midline or depression point on the sternum. NOTE: Use the round reference electrode and place it at FML-1L.

FML-1bTL is located in the 2nd intercostal space on a line between the lateral insertion of the sternocleidomastoid muscle and the nipple. It is approximately 3-3½ thumb widths from the midline. NOTE: Use the round reference electrode and place it at FML-1L.

FML-1cTL is located in the 3rd intercostal space approximately 3½ thumb widths lateral from the midline. NOTE: Use the round reference electrode and place it at FML-1L.

FML-2aTL is located in the depression on the lower border of the clavicle, 2 thumb-widths lateral to the midline. The 2 thumb-width line is located midway between the midline and the mamillary line. NOTE: Use the round reference electrode and place it 2 thumb-widths lateral to the midline of the spine on the back in the lowest intercostal space.

FML-2aL is located in the depression on the lower border of the clavicle, 2 thumb-widths lateral to the midline. The 2 thumb-width line is located midway between the midline and the mamillary line.

FML-2bL is located on the lateral aspect of the chest, in the first intercostal space, 6 thumb-widths lateral to the midline, 1 thumb-width inferior to FML-2c.

FML-2cL is located on the antero-lateral aspect of the chest, below the lateral extremity of the clavicle, 6 thumb-widths lateral to the midline, in the center of the hollow of the delto-pectoral triangle. Ask the patient to extend their hand forwards while you apply resistance to their hand, in order to emphasize the delto-pectoral triangle, and locate FML-2c at its center.

FML-3aL is located on the antero-lateral aspect of the upper arm, 3 thumb-widths inferior to the axillary fold and 6 thumb-widths superior to FML-4, in the depression between the lateral border of the biceps brachii muscle and the shaft of the humerus.

Divide the distance between the axillary fold and the cubital crease of the elbow into equal thirds. FML-3a is at the junction of the upper and middle third.

FML-3bL is located on the antero-lateral aspect of the upper arm, 4 thumb-widths inferior to the axillary fold and 5 thumb-widths superior to FML-4, in the depression between the lateral border of the biceps brachii muscle and the shaft of the humerus.

FML-4L is located on the cubital crease of the elbow, in the depression at the radial side of the tendon of biceps brachii.

FML-5L is located by moving from the wrist up the forearm along the flexor carpi radialis to the point where the brachioradialis is encountered.

FML-6aL is located on the radial artery, approximately 2½ inches above the wrist crease or 1 inch above the beginning of the styloid process of the radius bone. It is at the junction formed by the tendon of the brachioradialis and the flexor digitirum superficialis muscles.

FML-6dL is located approximately 1 inch proximal from the distal transverse wrist crease on the medial edge of the styloid process of the radius (palmar aspect of the hand).

FML-6eL is located at the lateral end of the distal wrist crease at the base of the palm. It is directly proximal to the lateral edge of the scaphoid's tubercle.

FML-7aL is located between the scaphoid and trapezium bones directly distal to the tubercle of the scaphoid.

FML-7bL is located at the proximal diaphyseal end of the first metacarpal bone, palmar aspect of the hand.

FML-7cL is located at the distal diaphyseal end of the 1st metacarpal bone on its ulnar side (palmar surface of the hand).

FML-8aL is located between the radius and navicular bones on the ulnar side of the extensor pollicis longus tendon.

FML-8bL is located at the distal diaphyseal end of the proximal phalanx of the thumb on its radial side. It is measured on a 45 degree angle with the probe pointing distally.

FML-8cL is located at the proximal diaphyseal end of the metacarpal phalanx of the thumb on its ulnar side (dorsal aspect of the hand). It is measured on a 45-degree angle with the probe pointing proximally.

FML-8dL is located at the distal diaphyseal end of the basal (proximal) phalanx of the thumb on its ulnar side (dorsal aspect of the hand). It is measured on a 45-degree angle with the probe pointing distally.

FML-8eL is located at the proximal diaphyseal end of the distal phalanx of the thumb (dorsal aspect). It is measured on a 45-degree angle with the probe pointing proximally.

FML-8fL is located at the distal diaphyseal end of the nail phalanx of the thumb on its ulnar side. It is measured on a 90-degree angle on the side of the finger with the probe on a horizontal plane with that of the fingernail.

FML-9L is located at the proximal diaphyseal end of the middle phalanx of the second finger on its ulnar side (dorsal aspect of the hand). It is measured on a 45 degree angle with the probe pointing proximally.

FML-10L is located at the proximal diaphyseal end of the middle phalanx of the 3rd finger on its radial side (dorsal aspect of the hand). It is measured on a 45 degree angle with the probe pointing proximally.

FML-11aL is located at the distal diaphyseal end of the ungual phalanx of the 4th finger on its ulnar side (dorsal aspect of the hand). It is measured on a 90 degree angle on the side of the finger.

FML-11bL is located at the proximal diaphyseal end of the middle phalanx of the 4th finger on its ulnar side (dorsal aspect of the hand). It is measured on a 45 degree angle with the probe pointing proximally.

FML-12aL is located at the distal diaphyseal end of the proximal phalanx of the little (5th) finger on its radial side (dorsal aspect of the hand). It is measured on a 45 degree angle with the probe pointing distally.

FML-12bL is located at the proximal diaphyseal end of the basal phalanx of the 5th finger on its ulnar side. It is measured on a 45 degree angle with the probe pointing proximally.

FML-12cL is located at the distal diaphyseal end of the nail phalanx of the 5th finger on its ulnar side (dorsal aspect of the hand). It is measured on a 90 degree angle on the side of the finger with the probe on a horizontal plane with that of the fingernail.

Desirably, software running on the computer system 104 is programmed to assist an operator during data acquisition. For example, the screen 112 may display a visual anatomical schematic having a highlighted interrogation point overlay that helps the device operator identify and place the interrogation probe 120. The screen image desirably changes as required to inform the operator of the desired interrogation point for each point of interest during a data acquisition series. A user-perceptible output, such as a low level modulated tone, may be produced to provide real-time feedback to the device operator to verify completion of an acceptable measurement. The conductance measurement profile for each conductance measurement may be displayed visually on the monitor 112. In use of a currently preferred device 100, the conductance value is sampled 25 times per second during each conductivity measurement.

Further, it is currently preferred for a computer-applied algorithm to control probe pressure to insure accurate and consistent measurements. Thus, the pressure applied to the skin surface during operation of the probe is reproducible and independent of operator force. The computer desirably implements threshold curves during electrode tip contact that adjust probe pressure in real-time to assure accurate readings and to prevent erroneous readings. After the measurement session is completed, the computer system 104 may store the data for post processing.

Figure 4:
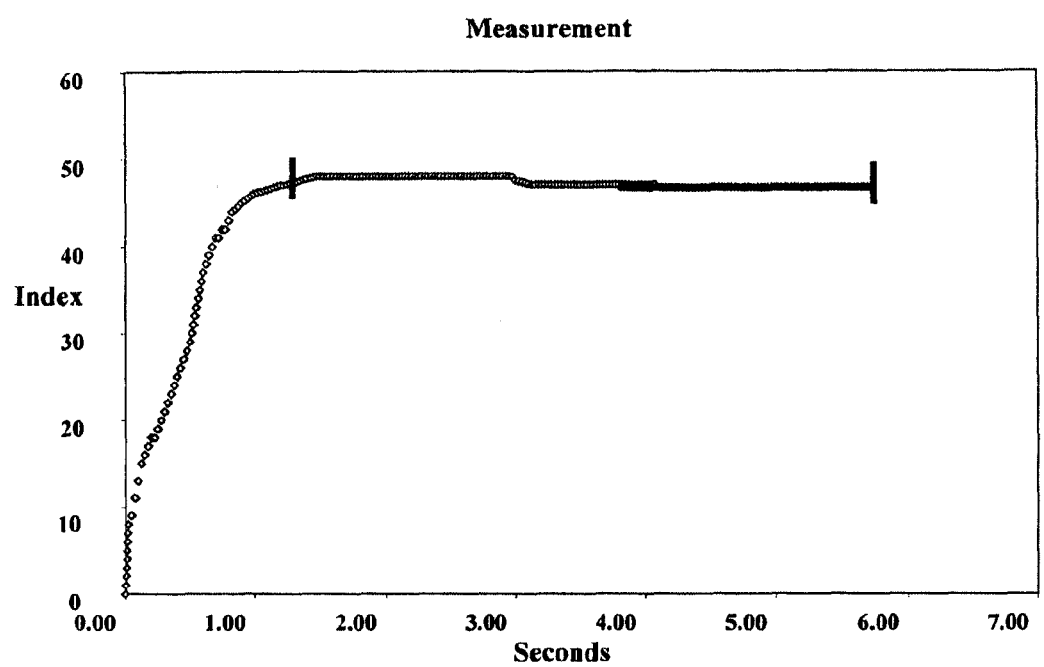
FIG. 4 is a representative plot of a conductivity data-set obtained during measurement of conductivity between a first point and a second point on the surface of a medical patient.

A representative plot of a data-set obtained during time-based measurement of conductivity at an interrogation point is presented in FIG. 4. In FIG. 4, the x axis represents time and the y axis represents measured Conductivity Index. Conductivity Index is defined as measured conductance equivalent to resistance from 1K ohms to 999K ohms at a nominal 1.2 or 2.4 volts. Firmware in the device 104 holds current steady at 10 microAmps, measures the voltage and then calculates the conductance. The software/firmware of computer system 104 desirably employs an algorithm that increases probe pressure until the conductivity index shows a zero slope. The algorithm then commands constant probe pressure for a period of time, such as for 5 seconds. In use of the presently preferred electrical interrogation probe, the Drop PWM (pulse width modulation) Rate variable of the computer algorithm is desirably set to zero. Such a zero value keeps the nominal pressure at the electrode tip constant after zero slope is reached. Electrical conductivity is measured between the interrogation probe and reference probe during a time interval as a data-set, and this information is passed to the computer system 104. The measured conductance is plotted as the Conductivity Index normalized on a scale of 0 to 100.

Eight attributes that may be parsed from a data-set, such as illustrated in FIG. 4, and which describe certain portions of such plot are defined as follows: Base Max is the maximum conductivity index value after zero slope is attained. Base Min is the minimum conductivity index value after zero slope is attained. Rise is the angle between the starting conductivity index and the conductivity index at zero slope. Fall is the angle between the conductivity index at the zero slope point and the conductivity index at the end of measurement. Drop is the difference between the Base Max and the Base Min. Area under the curve to zero slope is the percentage of the area under the curve from start to zero slope as compared to the total possible area from start to zero slope. Area under the curve from zero slope is the percentage of the area under the curve from zero slope to end of measurement as compared to the total possible area from zero slope to end of measurement. Area under the curve total is the percentage of the area under the curve from start of measurement to end of measurement as compared to the total possible area from start of measurement to end of measurement.

Acceptability of measurements may be determined by the system 104, and the clinician may receive perceptible feedback from the computer system 104 to confirm satisfactory completion of a data collection operation. Factors that may be evaluated to determine if data is collected successfully include: 1) Rise in conductivity to a zero slope, computer control. 2) Continued signal measurement thru the sustain timeout value without unexpected fluctuations, computer control and operator control. 3) If the blue line indicating zero slope doesn't appear within the first 2 seconds, the measurement should be repeated, operator control. 4) Excessive drop values repeated to confirm, operator control.

Failed measurements include: 1) Premature zero slope—machine control. 2) Excessive rise or drop after zero slope—machine control. 3) Low conductivity measurement as first measure especially if no other low conductivity measurements operator control. 4) No probe reset at first contact—operator control.

Figure 5:
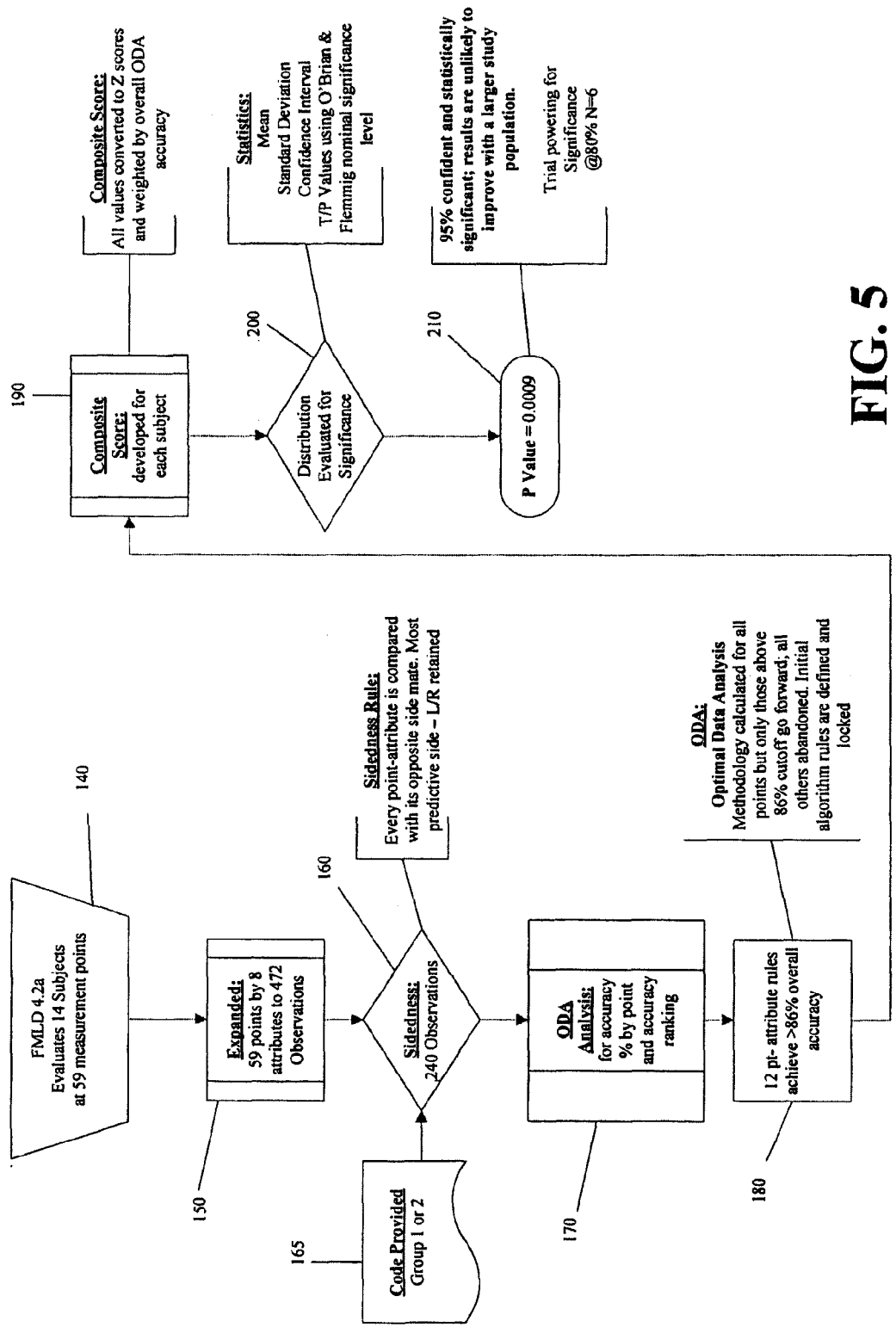
FIG. 5 is a flow chart illustrating a methodology to determine predictive rules including a disease-side bias.
Figure 6:
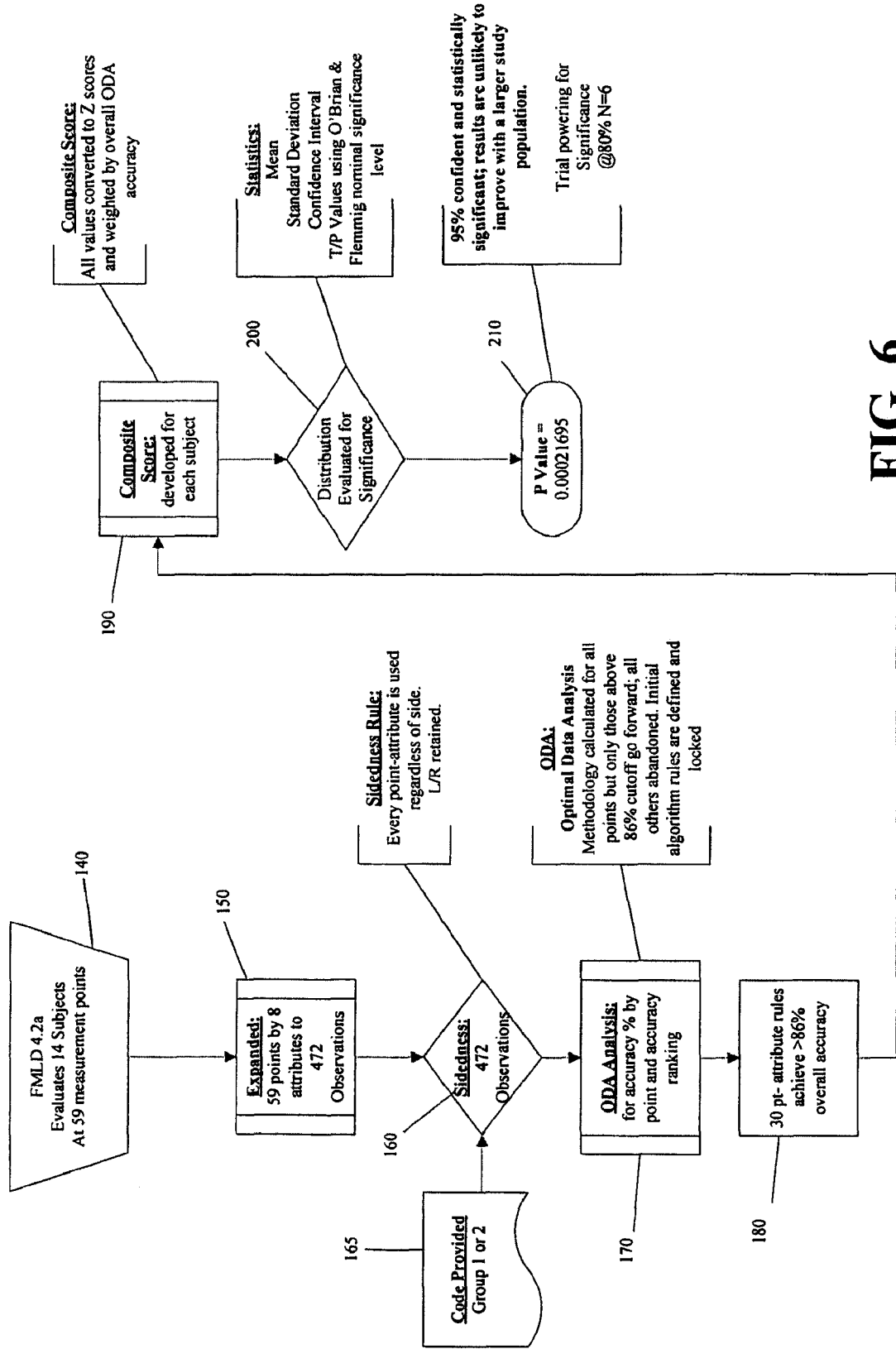
FIG. 6 is a flow chart illustrating a methodology to determine predictive rules without regard for a disease-side bias.

FIGS. 5 and 6 set forth operable methods to determine rule-sets for point-attribute data effective to diagnosis a disease condition in a patient. A rule-set including point-attribute threshold criteria may be determined by obtaining conductivity data-sets at one or more points on the body of each subject from two arm groups of sample subjects. One arm group should be diagnosed as having the disease, and the other group should be free of the disease. Conductivity measurements may be made blind to knowledge of the subject' arm group. The conductivity data can be expanded to a plurality of point-attributes for consideration of predictive capability with visibility to arm group. Accuracy, or predictive capacity, for each point-attribute may be determined by comparing "disease" data to "disease-free" data. A composite score may be developed from relevant point-attribute information.

With reference to FIG. 5, time-based conductivity measurements for 14 subjects were taken at 59 points, as indicated at 140. Measurement were blind to subject's group membership. At 150, the obtained data was expanded to 472 point-attributes.

Lung cancer often exhibits a side-bias, with dominant presence on one side (lung) of the body. Therefore, data analysis can include a determination of disease-sidedness based upon conductivity values. The data analysis presented in FIG. 5 included only 240 point-attributes. The most predictive side of the sample's body was determined based upon lower conductivity, and all point conductivity data from the opposite body side was discarded. The method presented in FIG. 6 included evaluation of all 472 point-attributes.

At 165, the blind was removed and Optimal Data Analysis (ODA) was performed at 170. ODA is a tool that evaluates the discrimination capability of all point attribute combinations. Overall ODA accuracy is the fraction of cases a point attribute combination correctly determined as malignant or benign. At 180 in FIG. 5, it was determined that threshold values existed for 12 point-attributes that satisfied a threshold criteria of greater than about 83% accuracy for indicating presence of lung cancer. At 180 in FIG. 6, it was determined that threshold values existed for 30 point-attributes that satisfied a threshold criteria of greater than about 86% accuracy for indicating presence of lung cancer. The cutoff at 0.8571 was arbitrary—no clinical importance was associated with this cutoff. Either a higher or a lower overall ODA accuracy criteria could have been used.

A z-score is one way to adjust factors to make them of equal weight. For example, Base Max ranges from 0 to 100 and AUC total ranges from 0 to 1. If we want to combine a Base Max score with an AUC total score and each have an equal weight, we use z-scores. The z-score is calculated by taking the measurement value and subtracting the mean and dividing by the standard deviation. (Value-Mean)/Standard deviation. The composite score is developed by adding each z-score multiplied by total accuracy and dividing by the sum of all of the weights.

A composite score for each subject was calculated using z-scores as indicated at 190. With reference to FIGS. 6 and 8, there were 30 point attribute combinations that had accuracy above 0.8571. In such case, the composite is developed as follows. Composite Score=[(AUG from 0 slope at FML2bR z-score)(0.8571)+(AUC total at FML6aL z-score)(0.8571)+ . . . +(base rise at FML11aL z-score)(0.8571)]/[0.8571(26)+ 0.9286(4)]. The data distribution may be evaluated according to data parameters indicated at 200. A confidence level may be determined as indicated at 210.

For this set of 14 subjects using the 30 point-attributes above 0.8571 there was perfect discrimination, that is all benign subjects had composite scores above a threshold value of 0.200 and all malignant subjects had composite scores below the same threshold value. The composite score threshold is defined as the value of a composite score that is below all benign subject composite scores and above all malignant composite scores. The composite score threshold value determined above can then be used to determine whether a subject from a similar population is likely malignant or benign based on whether the subject's composite score is above or below its corresponding threshold value.

In general, low conductivity suggests the presence of cancer. The "direction of low conductivity" set forth in FIG. 8 indicates whether low or high values of the evaluated point-attribute indicate cancer or low conductivity. This is obvious for most point attributes, but not obvious for base drop.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method to diagnose lung cancer in a medical patient, the method comprising:
providing a measurement device operable to measure conductivity between at least one reference point and at least one interrogation point on the body of a patient;
measuring the conductivity between at least one reference point and at least one interrogation point to obtain at least one data set;
comparing at least one value obtained from the at least one data set to at least one value in a previously-determined corresponding data set to assess the likelihood of the patient having lung cancer, wherein the measurement device is configured to provide computerized control of contact pressure between a measurement electrode tip and the surface of the body of the patient, and increasing the contact pressure between the measurement electrode tip and the surface of the body of the patient until a plot of a conductivity index over time exhibits a slope at or near zero.

2. The method of claim 1, wherein the step of measuring the conductivity comprises measuring the conductivity between the at least one reference point and the at least one interrogation point to obtain at least one data set as a function of time.

3. The method of claim 1, wherein the at least one value in a previously-determined corresponding data set comprises a threshold value indicative of a likelihood of the patient having lung cancer.

4. The method of claim 1, wherein the step of increasing the contact pressure between the measurement electrode tip and the surface of the body is automatically performed by the measurement device.

5. The method of claim 4, wherein the measurement device is further configured to, upon detecting that a plot of the conductivity index over time exhibits a slope at or near zero, automatically maintain the contact pressure substantially constant over a period of time.

6. The method of claim 1, further comprising measuring the conductivity between at least one second reference point and a plurality of interrogation points to obtain a plurality of data sets.

7. The method of claim 6, wherein each of the plurality of data sets comprises conductivity values as a function of time.

8. The method of claim 1, further comprising developing a composite score for a patient indicative of a likelihood of the patient having lung cancer.

9. The method of claim 8, wherein the composite score is developed by converting a portion of obtained point-attribute values to corresponding z-scores, and combining the z-scores.

10. A system for assisting in making a diagnosis of a disease condition in a medical patient, the system comprising:

a measurement device in communication with the computer assembly and configured to measure conductivity of the body of a patient between at least one ground point and at least one measurement point to obtain a conductivity data set corresponding to each such measurement, wherein the measurement device is configured to increase the contact pressure between a tip of the measurement device and the surface of the body of the patient until a plot of a conductivity index over time exhibits a slope at or near zero;

an extraction module operating on a processor of the computer assembly to extract point-attribute values from at least one data set; and a comparison module operating on a processor of the computer assembly to compare at least one attribute value obtained from at least one data set to a previously determined data set to provide an indication of whether the patient likely has a disease condition.

11. The system of claim 10, further comprising a conversion module to convert a portion of obtained point-attribute values to corresponding z-scores.

12. The system of claim 11, wherein the conversion module is further configured to weight each z-score by a corresponding predetermined accuracy and combine each weighted z-score to develop a composite score for a patient.

13. The system of claim 10, wherein the system is configured to provide a composite score displayable on the display terminal that provides an indication of a likelihood that the patient has the disease condition.

14. The system of claim 10, wherein the disease condition comprises cancer.

15. The system of claim 10, wherein the measurement device is configured to measure conductivity of the body of a patient between at least one ground point and at least one measurement point as a function of time.

16. The system of claim 10, wherein the comparison module is configured to compare at least one attribute value obtained from at least one data set to a previously determined corresponding attribute threshold to provide an indication of whether the patient likely has a disease condition.

17. The system of claim 16, wherein the comparison module is configured to compare at least one attribute value obtained from at least one data set to the previously determined corresponding attribute threshold in a table look-up operation to provide an indication of whether the patient likely has a disease condition.

18. The system of claim 10, wherein the measurement device is configured to provide computer control of contact pressure between a measurement electrode tip and a surface of the body at a measurement point.

19. The system of claim 18, wherein the computer control comprises real-time conductivity measurement in a feedback loop effective to adjust the contact pressure.

20. The system of claim 10, wherein the system is configured to display visible prompts on the display terminal corresponding to ground and measurement points.

* * * * *